US008784382B2

(12) United States Patent
McGuckin, Jr. et al.

(10) Patent No.: US 8,784,382 B2
(45) Date of Patent: Jul. 22, 2014

(54) HOLLOW CURVED SUPERELASTIC MEDICAL NEEDLE AND METHOD

(75) Inventors: James F. McGuckin, Jr., Radnor, PA (US); Robert L. Pakter, Tucson, AZ (US); Edward J. Morris, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/285,620

(22) Filed: Oct. 31, 2011
(Under 37 CFR 1.47)

(65) Prior Publication Data

US 2012/0046664 A1 Feb. 23, 2012

Related U.S. Application Data

(60) Division of application No. 12/641,117, filed on Dec. 17, 2009, now Pat. No. 8,048,030, which is a division of application No. 12/255,990, filed on Oct. 22, 2008, now Pat. No. 8,052,661, which is a continuation of application No. 11/281,151, filed on Nov. 17, 2005, now abandoned, which is a continuation of application No. 10/678,774, filed on Oct. 3, 2003, now abandoned, which is a continuation of application No. 10/201,112, filed on Jul. 22, 2002, now abandoned, which is a continuation of application No. 09/668,067, filed on Sep. 22, 2000, now Pat. No. 6,425,887, which is a division of application No. 09/457,844, filed on Dec. 9, 1999, now Pat. No. 6,592,559.

(60) Provisional application No. 60/111,624, filed on Dec. 9, 1998, provisional application No. 60/130,597, filed on Apr. 22, 1999.

(51) Int. Cl.
*A61M 5/178* (2006.01)

(52) U.S. Cl.
USPC .................................................... 604/164.01

(58) Field of Classification Search
USPC .............. 604/272, 204, 117, 273, 274, 93.01, 604/164.01
See application file for complete search history.

(56) References Cited

U.S. PATENT DOCUMENTS

| 2,219,605 | A | | 6/1938 | Turkel |
| 2,590,895 | A | | 11/1949 | Scarpellino |
| 4,013,080 | A | * | 3/1977 | Froning ................... 604/165.01 |
| 4,343,306 | A | | 8/1982 | Mericle |

(Continued)

FOREIGN PATENT DOCUMENTS

| EP | 0550258 | 7/1996 |
| EP | 0769272 | 4/1997 |
| WO | WO 96/27328 | 9/1996 |

*Primary Examiner* — Manuel Mendez
(74) *Attorney, Agent, or Firm* — Woodard, Emhardt, Moriarty, McNett & Henry LLP

(57) ABSTRACT

A needle assembly 10 compromising an infusion needle 11 that includes a needle cannula 13 made of a superelastic material such as Nitinol. The needle cannula is cold-worked or heat annealed to produce a preformed bend 16 that can be straightened within passageway 21 of a coaxial outer cannula 12 for introduction into the body of a patient. Upon deployment from the outer cannula, the needle cannula substantially returns to the preformed configuration for the introduction or extraction of materials at areas lateral to the entry path of the needle assembly. The needle assembly can compromise a plurality of needle cannulae than can be variably arranged or configured for attaining a desired infusion pattern.

13 Claims, 11 Drawing Sheets

(56) References Cited

U.S. PATENT DOCUMENTS

| | | | | |
|---|---|---|---|---|
| 4,396,022 A | * | 8/1983 | Marx | 600/571 |
| 4,403,617 A | | 9/1983 | Tretinyak | |
| 4,511,356 A | | 4/1985 | Froning et al. | |
| 4,518,383 A | | 5/1985 | Evans | |
| 4,616,656 A | | 10/1986 | Nicholson et al. | |
| 4,769,005 A | | 9/1988 | Ginsburg et al. | |
| 4,799,495 A | | 1/1989 | Hawkins et al. | |
| 4,846,799 A | | 7/1989 | Tanaka et al. | |
| 4,926,860 A | * | 5/1990 | Stice et al. | 606/144 |
| 4,958,901 A | | 9/1990 | Coombs | |
| 4,969,888 A | | 11/1990 | Scholten et al. | |
| 5,026,350 A | | 6/1991 | Tanaka et al. | |
| 5,031,634 A | | 7/1991 | Simon | |
| 5,067,957 A | | 11/1991 | Jervis | |
| 5,098,400 A | | 3/1992 | Crouse et al. | |
| 5,108,404 A | | 4/1992 | Scholten et al. | |
| 5,219,358 A | | 6/1993 | Bendel et al. | |
| 5,221,269 A | | 6/1993 | Miller et al. | |
| 5,231,989 A | | 8/1993 | Middleman et al. | |
| 5,238,004 A | | 8/1993 | Sahatjian et al. | |
| 5,242,448 A | | 9/1993 | Pettine et al. | |
| 5,243,996 A | | 9/1993 | Hall | |
| 5,295,493 A | | 3/1994 | Radisch, Jr. | |
| 5,345,937 A | | 9/1994 | Middleman et al. | |
| 5,354,279 A | * | 10/1994 | Hofling | 604/164.12 |
| 5,419,777 A | * | 5/1995 | Hofling | 604/264 |
| 5,464,395 A | | 11/1995 | Faxon et al. | |
| 5,486,183 A | | 1/1996 | Middleman et al. | |
| 5,533,982 A | | 7/1996 | Rizk et al. | |
| 5,542,434 A | | 8/1996 | Imran et al. | |
| 5,556,410 A | | 9/1996 | Mittermeir et al. | |
| 5,573,542 A | | 11/1996 | Stevens | |
| 5,597,378 A | | 1/1997 | Jervis | |
| 5,601,572 A | | 2/1997 | Middleman et al. | |
| 5,607,389 A | | 3/1997 | Edwards et al. | |
| 5,628,734 A | | 5/1997 | Hatfalvi | |
| 5,636,641 A | | 6/1997 | Fariabi | |
| 5,741,278 A | | 4/1998 | Stevens | |
| 5,766,218 A | | 6/1998 | Arnott | |
| 5,853,423 A | | 12/1998 | McGregor et al. | |
| 5,895,395 A | | 4/1999 | Yeung | |
| 5,964,796 A | * | 10/1999 | Imran | 607/122 |
| 6,059,766 A | * | 5/2000 | Greff | 604/515 |
| 6,143,004 A | | 11/2000 | Davis et al. | |
| 6,190,353 B1 | | 2/2001 | Makower et al. | |
| 6,217,554 B1 | | 4/2001 | Green | |
| 6,425,887 B1 | * | 7/2002 | McGuckin et al. | 604/272 |

* cited by examiner

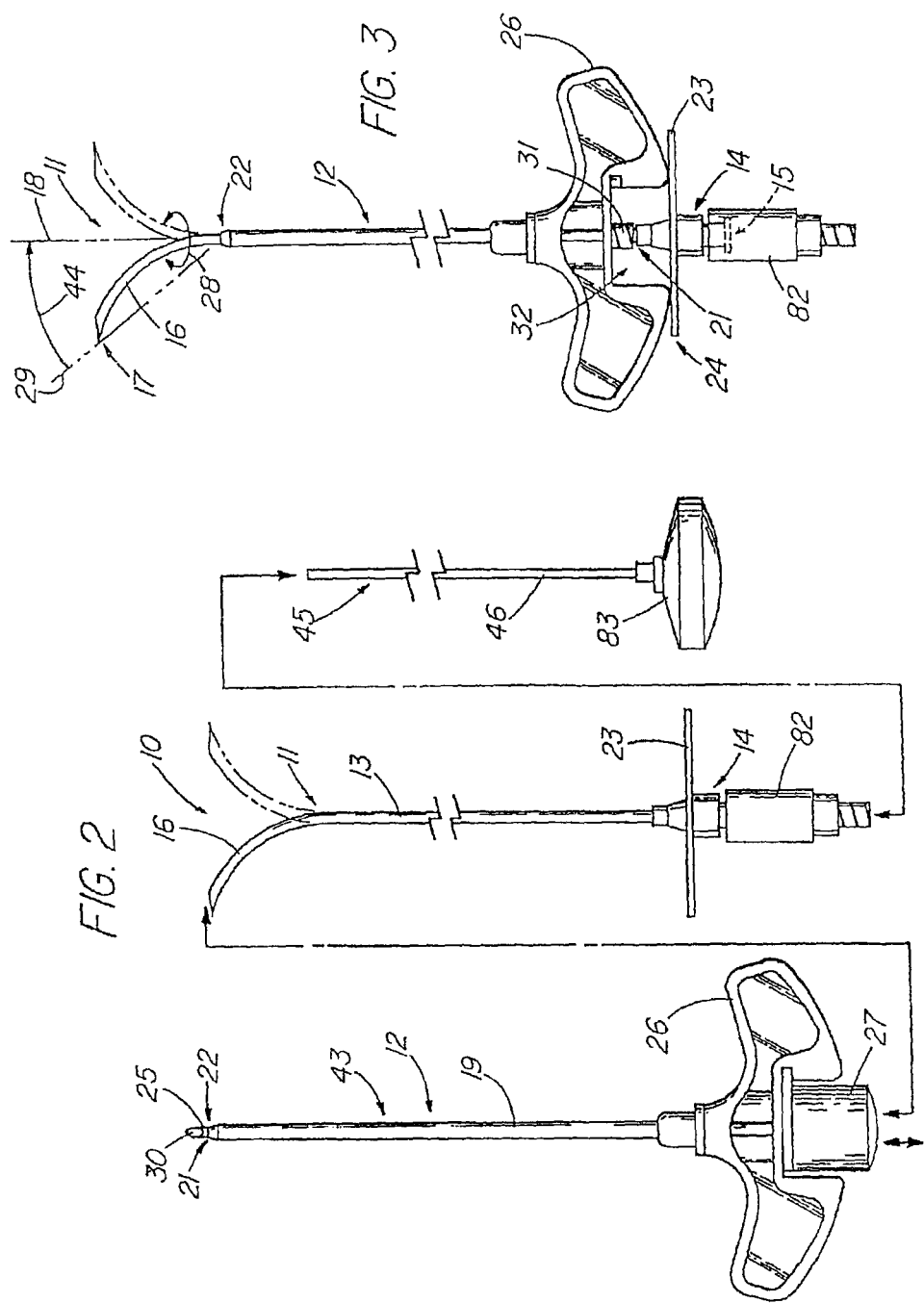

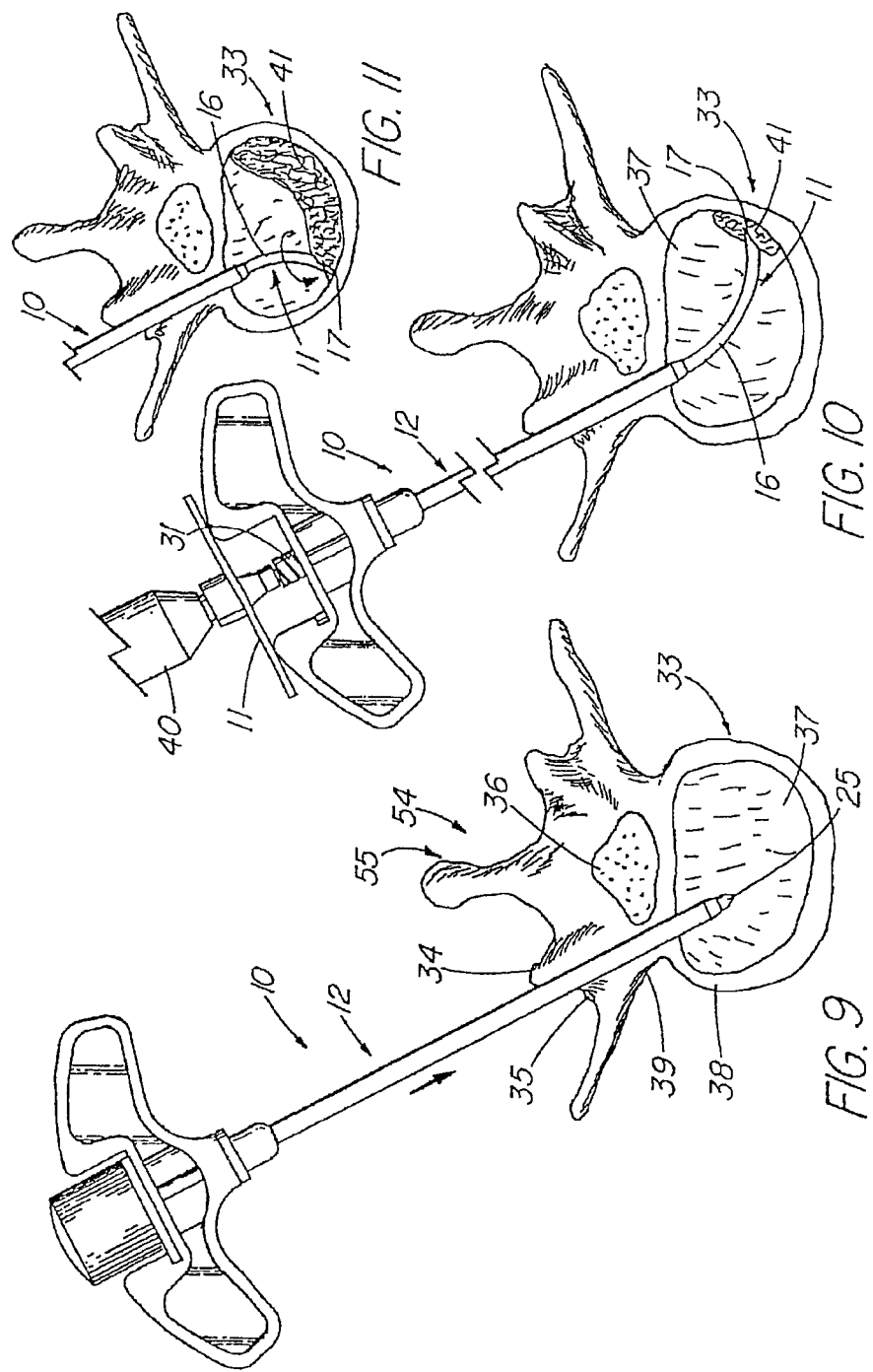

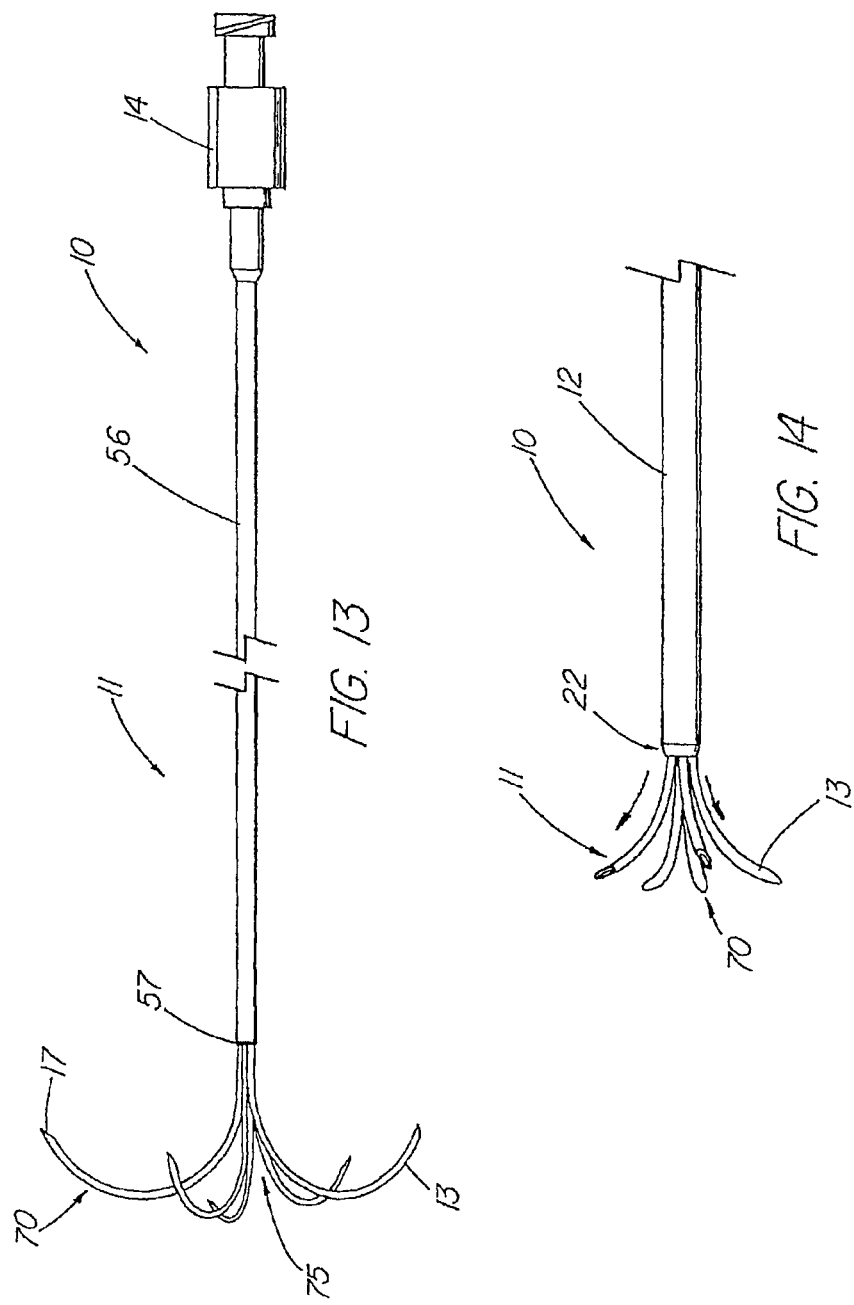

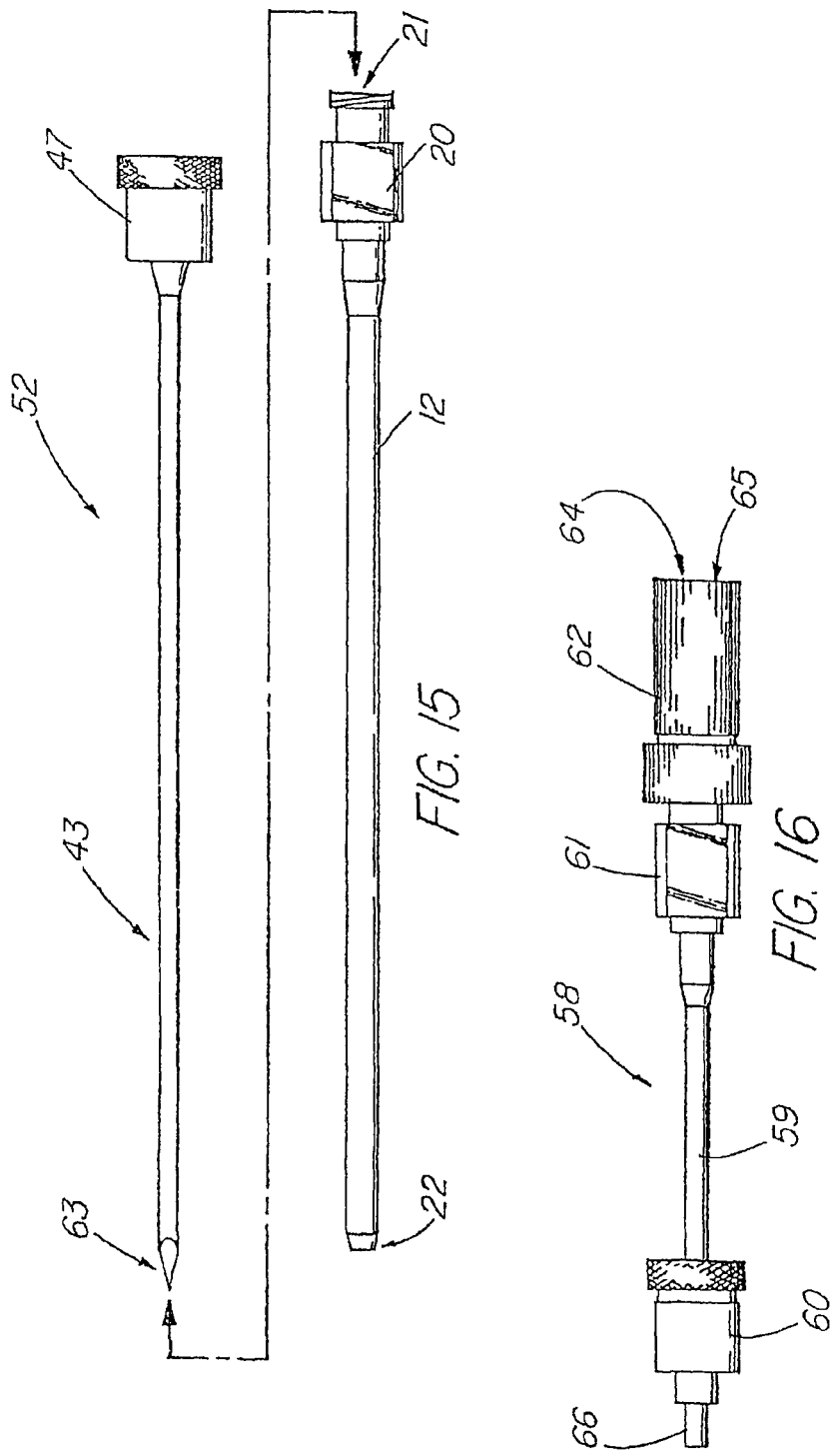

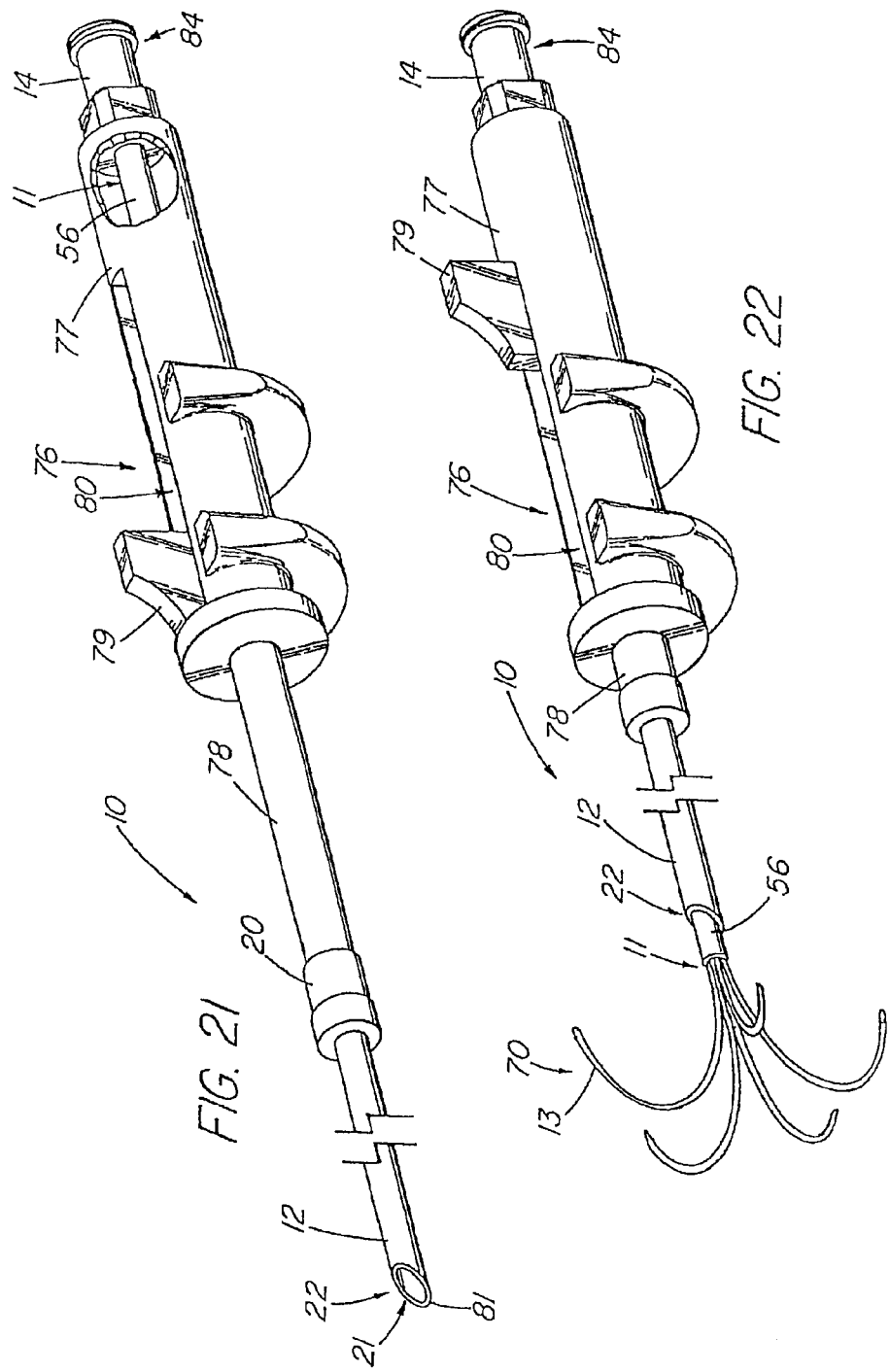

HOLLOW CURVED SUPERELASTIC MEDICAL NEEDLE AND METHOD

CROSS-REFERENCE TO RELATED APPLICATIONS

This application is a divisional of U.S. application Ser. No. 12/641,117, filed Dec. 17, 2009, now U.S. Pat. No. 8,048,030 issued Nov. 1, 2011 which is a divisional of U.S. patent application Ser. No. 12/255,990, filed Oct. 22, 2008, now U.S. Pat. No. 8,052,661 issued Nov. 8, 2011, which is a continuation of U.S. patent application Ser. No. 11/281,151, filed Nov. 17, 2005, now abandoned, which is a continuation of U.S. patent application Ser. No. 10/678,774, filed Oct. 3, 2003, now abandoned, which is a continuation of U.S. patent application Ser. No. 10/201,112, filed Jul. 22, 2002, now abandoned, which is a continuation of U.S. patent application Ser. No. 09/668,067, filed Sep. 22, 2000, now U.S. Pat. No. 6,425,887 issued Jul. 30, 2002, which is a divisional of U.S. patent application Ser. No. 09/457,844, filed on Dec. 9, 1999, now U.S. Pat. No. 6,592,559 issued Jul. 15, 2003, which claims the benefit of U.S. Provisional Patent Application Ser. Nos. 60/111,624, filed Dec. 9, 1998 and 60/130,597 filed Apr. 22, 1999, each of which is hereby incorporated herein by reference.

TECHNICAL FIELD

This invention relates generally to medical devices and more particularly to needles that are curved for indirect infusion access within the body.

BACKGROUND

Medical procedures involving the vertebrae are typically complicated because of the preciseness required to avoid both neural damage and injury to major blood vessels, as well as the indirect path that is usually required to access the treatment site.

This is certainly the case when performing a vertebroplasty, a procedure whereby bone cement, most commonly methyl methacrylate, is injected into a vertebral body to provide stabilization and/or pain relief in selected patients having a spinal condition such as osteolytic metastasis and myeioma, painful or aggressive hemangiome (benign lesions of the spine), or painful osteoporotic vertebral collapse.

Standard treatment practice depends on the region of the spine being treated. For the cervical vertebrae, anterolateral access is used with a 15 gauge needle. The large vessels adjacent to the vertebra are laterally manipulated by the radiologist to provide an access site between the vessels and the pharyngolarynx. An upward access route is required because the needle must be introduced below the mandible.

When accessing the thoracic or lumbar vertebrae, typically a large 10 gauge needle is used following a transpedicular or posterolateral approach. The transpedicular route is preferred to avoid spinal nerve injury and to decrease the probability of the cement leaking into tissues adjacent to the vertebral body.

To obtain complete fill of a damaged vertebral body, it is often required that a second transpedicular access be made from the opposite side. A single infusion usually cannot fill the entire target area because the needle tip cannot be redirected from the original plane of entry. Continued infusion of cement from the first access site will usually not result in an adequate infusion due to the tendency of the material to set before it fills all of the affected area, thereby becoming a baffle to itself. Furthermore, the thick density of the marrow and structures, such as veins, usually acts to impede free flow of the cement within the vertebral body.

Another concern during the procedure is accidental puncture of the these veins. Because vertebral veins lead directly to the lungs, there is a significant risk of pulmonary embolism if cement is accidentally introduced therein.

The inability to adequately maneuver the needle cannula tip within a body or around structures is a major limitation of the straight needle. Additional needle sticks to complete a medical procedure result in discomfort to the patient and additional risk of leakage and other complications.

To sufficiently access a vertebral body for complete infusion of cement, the needle tip must be capable of being deflected at significantly large angles from the original axis. This would require that the needle have a distal bend so that the needle could be rotated to selectively direct the material.

Rigid curved needles are well known for suturing applications; however, adding anything more than a slight bend to an infusion needle limits its access path and ability to deeply penetrate tissue, especially bone. For example, a rigid curved needle is unsuitable for use in a vertebroplasty procedure where the needle cannula must be driven through the bone and deep into the vertebral body using a relatively straight approach and maintained in place to avoid additional damage to the entry site. While the initial needle access must be done with a straight needle of sufficient strength to penetrate bone, the ideal approach would be to direct a lateral infusion of cement following needle penetration, and then to withdraw the needle along its original path.

Accomplishing this is problematic. The tissue density and resistance of the tissue to penetration at the treatment site can require that the inner infusion member be nearly as stiff as the outer piercing cannula. A certain degree of needle rigidity is required in order to be able to maneuver the needle and accurately direct flow of material.

While stainless steel needles having a slight distal bend are known, the amount of needle curvature necessary to provide adequate lateral infusion is not possible—the needle plasticly deforms once inside the outer restraining cannula and hence is unable to return resiliently to its preformed shape. Thus, a second needle access would still be required to provide adequate filling.

Other medical procedures present similar problems when a single straight needle is used. One example is tumor ablation where percutaneous ethanol injection is used to treat carcinoma of the liver and kidney. Originally introduced as a palliative treatment for inoperable hepatocellular carcinoma of the liver, ethanol injection has now been shown to have curative potential comparable to resection in many patients, especially for smaller tumors.

Practice has been to inject ethanol directly into masses using a straight needle and to allow the ethanol to infuse from one or more side holes into the tissue. The problem is that the infusion may not penetrate any deeper than the needle tract; thus portions of the tumor are not effectively treated. It is desirable to provide a device for more effective infusion of ethanol into the tumor mass.

SUMMARY OF THE INVENTION

The foregoing problems are solved and a technical advance is achieved in an infusion needle made of rigid superelastic material and having at least one performed bend along the distal portion of its length. The needle is used as an inner cannula coaxially with a second hollow cannula for restraining the inner needle cannula in a substantially straight orientation during percutaneous introduction to the target site, whereby the inner needle cannula is deployed to resiliently return to its preformed configuration.

The ability of the preformed inner needle cannula to deflect laterally upon exiting the outer cannula allows the inner needle cannula to infuse or aspirate material at multiple points within different planes in the body as the inner infusion needle rotates about its longitudinal axis. This helps to reduce or eliminate the need for additional "sticks" with the outer cannula; it also allows the operator to make an entry from one direction, then to deploy the curved inner cannula to reach a site that cannot be accessed directly, such as where another structure lies along the access path, thereby blocking the target site.

The preferred material for the inner cannula is a superelastic, shape memory alloy such as sold under the trademark Nitinol (Ni—Ti); however, there are other non Ni Ti alloys that may be used. A Nitinol alloy is desirably selected that has properties whereby the temperature at which the martensitic to austenitic phase change occurs is lower than the working temperature of the device (i.e. room temperature).

As described in U.S. Pat. No. 5,597,378, incorporated herein by reference, a permanent bend may be heat set in a superelastic Nitinol cannula by maintaining the cannula in the desired final shape while subjecting it to a prescribed high temperature for a specific time period. The resulting cannula can be elastically manipulated far beyond the point at which stainless steel or other metals would experience plastic deformation. Nitinol and other superelastic materials when sufficiently deformed undergo a local phase change at the point of stress to what is called "stress-induced martensite" (SIM). When the stress is released, the material resiliently returns to the austenitic state.

A second method of imparting a permanent bend to the needle material is by a process commonly known as "cold working." Cold working involves mechanically overstressing or overbending the superelastic cannula. The material within the bending region undergoes a localized phase shift from austenite to martensite and does not fully return to its original shape. In the case of the cold-worked cannula, the result is a permanent curve about the bending zone which has been locked in to at least a partial martensitic crystalline state.

In contrast, when heat treating is used, the entire heat-annealed cannula is in a austenitic condition, even in the curved region, and is only temporarily transformed to martensite under sufficient bending stresses. Therefore, the flexural properties of the annealed cannula vary little across its length.

Conversely, the bend of a cold-worked cannula, which contains martensite, has increased resistance to deformation and therefore holds its shape better than the more flexible bend of the pure austenitic cannula This increased rigidity can be an advantage for certain clinical applications.

In one aspect of the invention, an introducer trocar or stylet is used with either the outer or inner needle cannula, depending on the luminate size of the needle, to facilitate access to tissue and/or prevent coring tissue into the distal tip of the needle device. The infusion needle or inner cannula is introduced through the outer cannula after access has been established and the trocar or stylet is removed.

Depending on the size of the cannulas, the degree of the preformed bend, or the method used to form the bend, the inner cannula or needle may slightly deform the outer cannula as the preformed bend present in the inner needle or cannula is constrained within the outer cannula. As a result, the outer cannula may be deflected a few degrees from its normal longitudinal axis at a point corresponding to the bend of the inner cannula. As the inner cannula is deployed from the outer cannula, the inner cannula deflects laterally until the entire region of the bend is unsheathed. The distal opening of the inner cannula is oriented at a large angle (preferably within the range of 60-90° from the original longitudinal axis when the inner needle is fully deployed.

The ability of the inner cannula to deflect at a significant angle from the original longitudinal axis has great utility in a number of applications where straight access is required followed by redirection of the distal opening. This deflection permits access to a different site without the necessity of withdrawing and reintroducing the needle.

A primary example of such a procedure is vertebroplasty in which infusion of the stabilizing cement with a straight needle often requires a second stick to provide complete filling to stabilize the vertebral body while avoiding damage to delicate structures such as veins. As with the standard single-needle procedure involving the thoracic or lumbar regions of the spine, a transpedicular approach is normally used whereby the larger outer needle cannula, such as a coaxial Jamshldi-type needle, is introduced into the damaged or diseased vertebral body. The outer needle includes an inner introducer trocar which is then replaced with a inner curved needle for infusion of the cement.

The ability of the curved needle to deflect laterally and rotate to reach multiple planes gives it a significant advantages over straight needles which have a limited range of movement. Because of this additional range of movement, the curved needle can usually complete the vertebroplasty procedure with a single access of the vertebral body. This avoids additional discomfort and risks to the patient, which include complications from leakage of cement or inadvertent infusion into non-target areas.

In addition to using the coaxial needle for infusion of cement as above, the device can also be adapted for aspirating material or serving as a conduit for the introduction of other devices. The apparatus may be used for a percutaneous corpectomy, a procedure which involves fusion and decompression of two or more vertebrae by first aspirating tissue from the damaged vertebral bodies, then introducing a prosthesis having a carbon fiber composite cage packed with bone graft material to serve as scaffolding for the affected vertebrae. Once the cage is properly positioned, methyl methacrylate or another suitable material is infused into the vertebral bodies to secure the prosthesis. The percutaneous corpectamy offers less trauma, and with the reinforcement cage, provides superior rigidity over a conventional corpectomy utilizing bone graft material alone.

In another aspect of the invention, the coaxial needle can be adapted for paraspinal use to inject medicaments within the neural canal or epidural space as part of management and/or diagnosis of pain. Preferably, the outer cannula has a tip adapted for piercing soft tissue. This outer needle cannula, preferably about twenty-one (21) gauge, is introduced percutaneously parallel to the spinal column along with an internal stylet with matched bevel to prevent coring tissue into the distal opening. The stylet is removed and the curved needle, about twenty-five (25) gauge, is inserted into the outer cannula. The needle assembly is then maneuvered to contact a nerve root during a diagnostic procedure to help recreate pain symptoms of the patient. The inner infusion needle also includes a stylet which is situated within the passageway of the needle as it is directed to the target site. The stylet is then removed from the infusion needle and medicaments, commonly steroids such as celestone (injected with lidocaine), kenalog, or methylprednisone are introduced to the treatment site. The inner needle is then withdrawn into the outer sheathing cannula and both are withdrawn from the patient.

Another use of the smaller gauge paraspinal needle is for diskography which consists of injecting a contrast agent (preferably nonionic contrast media) directly into the patient's disk to delineate the extent of any malformation or injury to the vertebral body.

Yet another aspect of the invention solves the problem of infusion of ethanol into a tumor mass by utilizing a plurality of curved needle cannulae deployed within an cannula introduced into the tumor where the curved needle cannulae radiate outward into an umbrella-shaped configuration. Infusion can take place at multiple points within the tumor to provide wider dispersion of the ethanol. Following treatment, the curved needle cannulae are withdrawn into the cannula and the device is removed from the patient.

In a related aspect, one or more needle cannulae are located proximal to the distal end of the infusion needle. These proximally-located cannulae allow infusion of medicaments at different points along the length of the device. By having multiple sets of needles arranged in the umbrella configuration, the volume of tissue treated is increased. The coaxial outer cannula includes a plurality of side apertures that allow the proximally-located needle cannulae to deploy after the infusion needle is placed at the desired location in the body and the outer cannula is withdrawn. An outer sheath over the coaxial outer cannula selectively exposes the side apertures to permit the appropriate alignment of needle cannulae and apertures when there are multiple rows of each.

The invention has applicability in any clinical situation where a straight approach is dictated and there is a need to avoid an obstructing structure (a large vessel, bowel loop, etc.) in the entry path, or the need to redirect the approach to a more lateral pathway to infuse medicaments or aspirate, such as to drain an abscess.

In addition to infusion or aspiration, the invention can provide a conduit for introducing and/or directing the path of other medical devices within the body such as radio-frequency ablation catheters or wire guides. This would allow a straight approach to a critical juncture whereafter the curved infusion needle can be deployed to precisely proceed to the desired anatomical site, especially in situations such as a luminal bifurcation or when access to an ostium is required.

Another use of the invention is to place the infusion needle in a bronchoscope or colonoscope which can serve as the outer constraining device. Under visualization, the inner needle then can be directed to perform a biopsy or other type of procedure.

BRIEF DESCRIPTION OF THE DRAWINGS

FIG. 2 is a top view of an outer needle cannula with an introducer trocar and the inner curved needle cannula;

FIG. 3 is a top view of the assembly of the inner curved needle cannula inside the outer needle cannula;

FIG. 9 is a partially sectional view depicting the apparatus of FIG. 2 being introduced into a vertebral body;

FIG. 10 is a partially sectional view similar to FIG. 9, depicting of the apparatus of FIG. 2 infusing cement into a vertebral body.

FIG. 11 is a broken, partially sectioned view similar to FIGS. 9 and 10, depicting of the apparatus of FIG. 2 infusing additional cement into a vertebral body.

FIG. 13 is a side view of the multi-directional infusion needle illustrated in of FIG. 12;

FIG. 14 is a broken, side view of the needle of FIG. 13 partially showing the needle deployed;

FIG. 15 is a side view of a trocar introducer used with the embodiment of FIG. 12;

FIG. 16 is a side view of the proximal assembly portion of the apparatus illustrated in FIG. 12;

FIG. 21 is an isometric view of a fifth embodiment of the present apparatus; and FIG. 22 is an isometric view similar to that of FIG. 21 showing the apparatus fully deployed.

DETAILED DESCRIPTION

Figure 1:
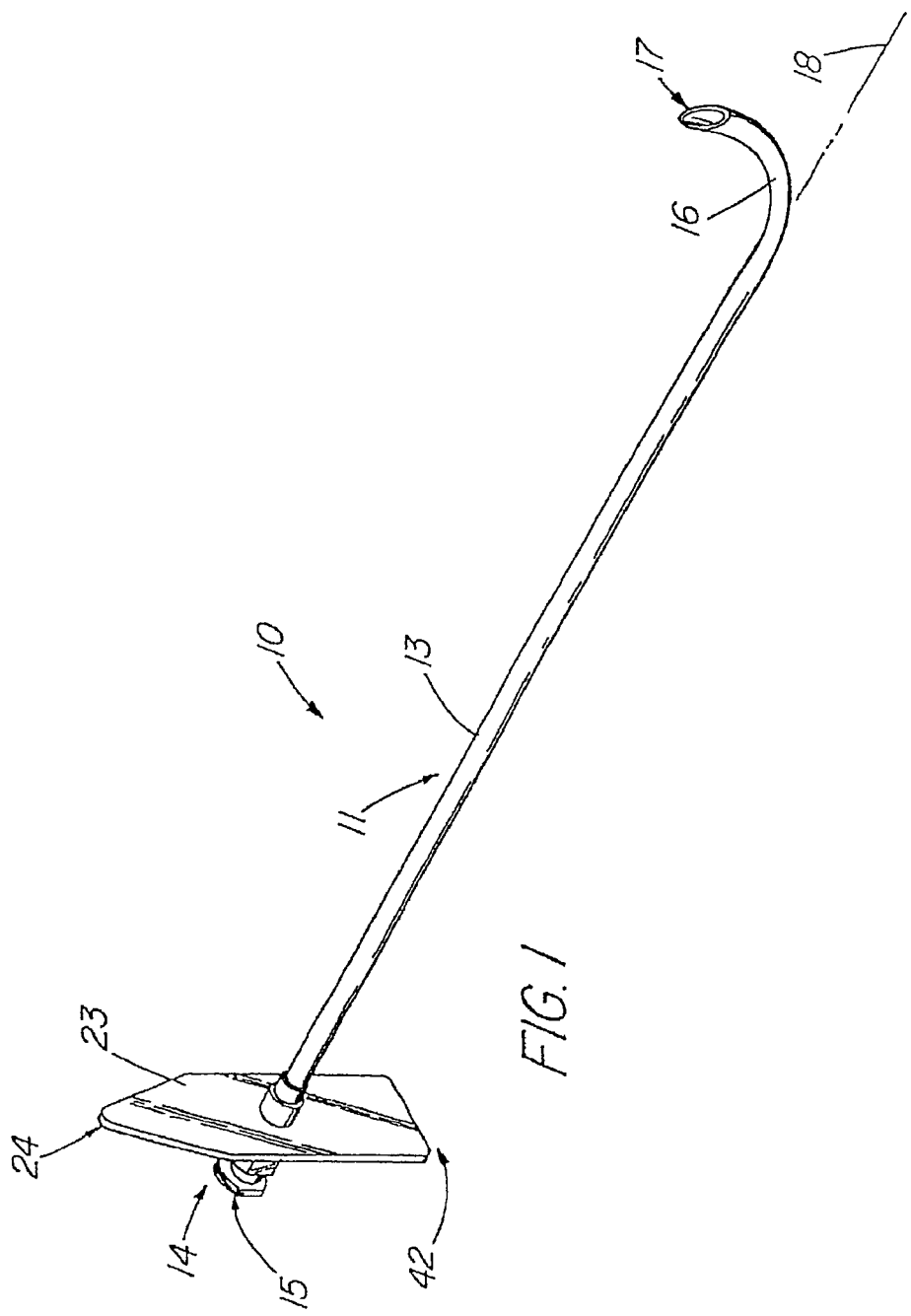
FIG. 1 is an isometric view of an illustrative embodiment of the curved needle inner cannula.

FIG. 1 depicts a needle assembly 10 comprising an infusion needle 11 with a preformed bend 16 for lateral infusion or aspiration of medicaments and other materials. As defined herein, the "needle assembly 10" can comprise infusion needle 11 alone or infusion needle 11 in combination with other components. The "infusion needle 11" as defined herein comprises one or more needle cannulae having a preformed bend 16.

The infusion needle 11 of FIG. 1 is comprised of a superelastic alloy needle cannula 13, preferably the alloy sold under the trademark Nitinol, that is soldered or otherwise affixed to a well-known needle hub 14 using one of a selected number of well-known techniques, including that of Hall described in U.S. Pat. No. 5,354,623 whose disclosure is expressly incorporated herein by reference, and a flange 23 which has a first tapered or pointed end 24 whose shape is readily distinguishable from the second, squared end 42.

First end 24 corresponds to the direction of preformed bend 16 in needle cannula 13 of infusion needle 11. Bend 16 is formed in the Nitinol needle cannula 13 by either the well-known process of deforming the cannula under extreme heat for a prescribed period of time, which produces a cannula entirely in the austenitic state, or by cold working the cannula, which involves applying a large amount of mechanical stress to deflect the 15 cannula well beyond the desired amount of permanent bend. Cold working permanently locks a crystalline structure in the bending zone into at least a partial martensitic condition while the unstressed portions of the cannula remain in the austenitic state.

Cold worked Ni—Ti alloys are discussed in "Linear Superelasticity In Cold-Worked Ni—Ti", (Zadno and Duerig) pp. 414 to 419, in *Engineering Aspects of Shape Memory Alloys*, Butterworth-Heineman, Boston, Mass. (Duerig et al, editors) which is incorporated herein by reference. In addition to Nitinol, superelastic or pseudoelastic copper alloys, such as Cu—Al—Ni, Cu—Al—Zi, and Cu—Zi, are available as alternative needle cannula materials. Flexible polymeric materials with sufficient rigidity for both deployment and shape memory to assume a desired curve may also be used in certain applications, either alone or in combination with reinforcing metal components such as a metal braid or tip.

Preformed bend 16 of infusion needle 11 forms a distal portion of needle cannula 13, preferably close to about 25% of the length of needle cannula 13 in the embodiment shown in FIG. 1. The large size of the infusion needle, preferably 10 to 18 gauge, makes this particular embodiment suitable for penetrating a vertebral body to perform a vertebroplasty or percutaneous corpectomy procedure. A more preferred range is 12 to 17 gauge, with the most preferred cannula size being 13 to 15 gauge.

With regard to a vertebroplasty and corpectomy procedures, the larger gauge cannula has both the strength to penetrate dense bone material as well as a sufficient lumen diameter to aspirate material from the vertebral body and to infuse highly viscous bone cement, such as methyl methacrylate. The preferred preformed bend 16 of the infusion needle 11 has a constant radius. For the embodiment of FIG. 1, the preferred radius of distal bend 16 is approximately 3.0 cm for a 13 gauge needle, and approximately 2.5 cm for a 14 gauge needle. Although the illustrative embodiment has a constant bend radius, an increasing or decreasing radius bend could be employed for certain clinical applications. Furthermore, it is possible to introduce more than one bend into the superelastic cannula for applications requiring a special needle configuration.

The primary purpose of using a Nitinol or other superelastic alloy cannula is that the cannula can be constrained into one shape during passage to the treatment site, then deployed into the preformed configuration without experiencing any plastic deformation.

FIG. 2 depicts a pair of needles to be used coaxially in that manner, including the infusion needle 11 of FIG. 1 and a coaxial outer cannula 12 for maintaining inner infusion needle 11 in a substantially straight configuration while being introduced to the treatment site. The embodiment depicted in FIG. 2 is Jamshidi-type needle (Manan Inc., Northbrook, Ill.) which is a two-part needle assembly 43, and is most commonly used for accessing dense, hard tissue such as bone, fibrous material, etc. Thus, it is well suited for penetrating the wall of a vertebral body wherein the infusion needle 11 can be deployed.

The two-part needle assembly 43 includes a coaxial outer cannula 12 having a stainless steel cannula 19 with an inner passageway 21 that is sufficiently large to accommodate inner infusion needle 11. For example, the standard 11 gauge Jamshidi-type needle suitable for accessing a vertebral body would be used with thirteen (13) gauge inner curved needle. Stainless steel cannula 19 is affixed proximally to a handle 26 and a connector hub 31 (shown in FIG. 3). The connector hub 31 receives the second part of the two-part needle assembly 43, the coaxial outer cannula introducer 52 which preferably comprises a trocar 25. The trocar hub 27 locks into handle 26 of coaxial outer cannula 12. The beveled tip 30 of trocar 25 extends approximately 5 mm beyond the distal tip 22 of coaxial outer cannula 12 and assists in penetration. Trocar 25 also serves to prevent the coaxial outer cannula 12 from coring a sample of bone or other material during access.

After outer needle assembly 43 has been directed to the target site, trocar 25 is removed from coaxial outer cannula 12 and infusion needle 11 is inserted into passageway 21 of the coaxial outer cannula 12, as shown in FIG. 3. To maintain openness of the infusion needle passageway 15 and to prevent tissue coring during deployment, an inner needle introducer stylet 46 can be introduced coaxially inside the infusion needle. Inner needle introducer stylet 45 includes a handle 83 and a shaft 46 which is made of a flexible, high-tensile, polymeric material such as polyetherethylketone (PEEK) to allow stylet 45 to assume the contour of preformed bend 16 after deployment.

Inner infusion needle 11 straightens as it is loaded into coaxial outer cannula 12. As the portion including preformed bend 16 of infusion needle 11 extends out from tip 22 of coaxial outer cannula 12 as depicted in FIG. 3, infusion needle 11 assumes the preformed shape due to the superelastic properties of needle cannula 13. For infusion, inner needle introducer stylet 52, which helps prevent coring of tissue into passageway 21 of coaxial outer cannula 12, is removed. The tapered or "arrow" end 24 of flange 23 of proximal hub 14 corresponds with the deflection plane 29 of infusion needle 11.

By maneuvering flange 28, the inner curved needle 13 can be rotated in either direction 28 to reorient the plane of deflection 29 and place the tip opening 17 at multiple locations within the area being treated.

In FIG. 3, tip 17 is deflected at an angle 44 of approximately 60° to 70° from the device longitudinal axis 18. This gives, for example, with a thirteen (13) gauge infusion needle 11, a lateral reach, measured from tip 17 to longitudinal axis 18, of nearly thirty (30) millimeters in any direction.

While the degree of deflection required is determined by the application and desired lateral reach of the device, it is also limited by the size of the cannula if the permanent bend is cold worked into the material. Cold working provides a stiffer bend which can be advantageous in certain applications such as vertebroplasty and biopsy of dense tissue; it is more difficult to permanently deform a larger gauge Nitinol cannula without application of extreme heat. For the embodiments contemplated, the angle of deflection 44 can encompass a range of 30° to 110°, with a preferred range of 40 to 90° for most applications.

Figure 4:
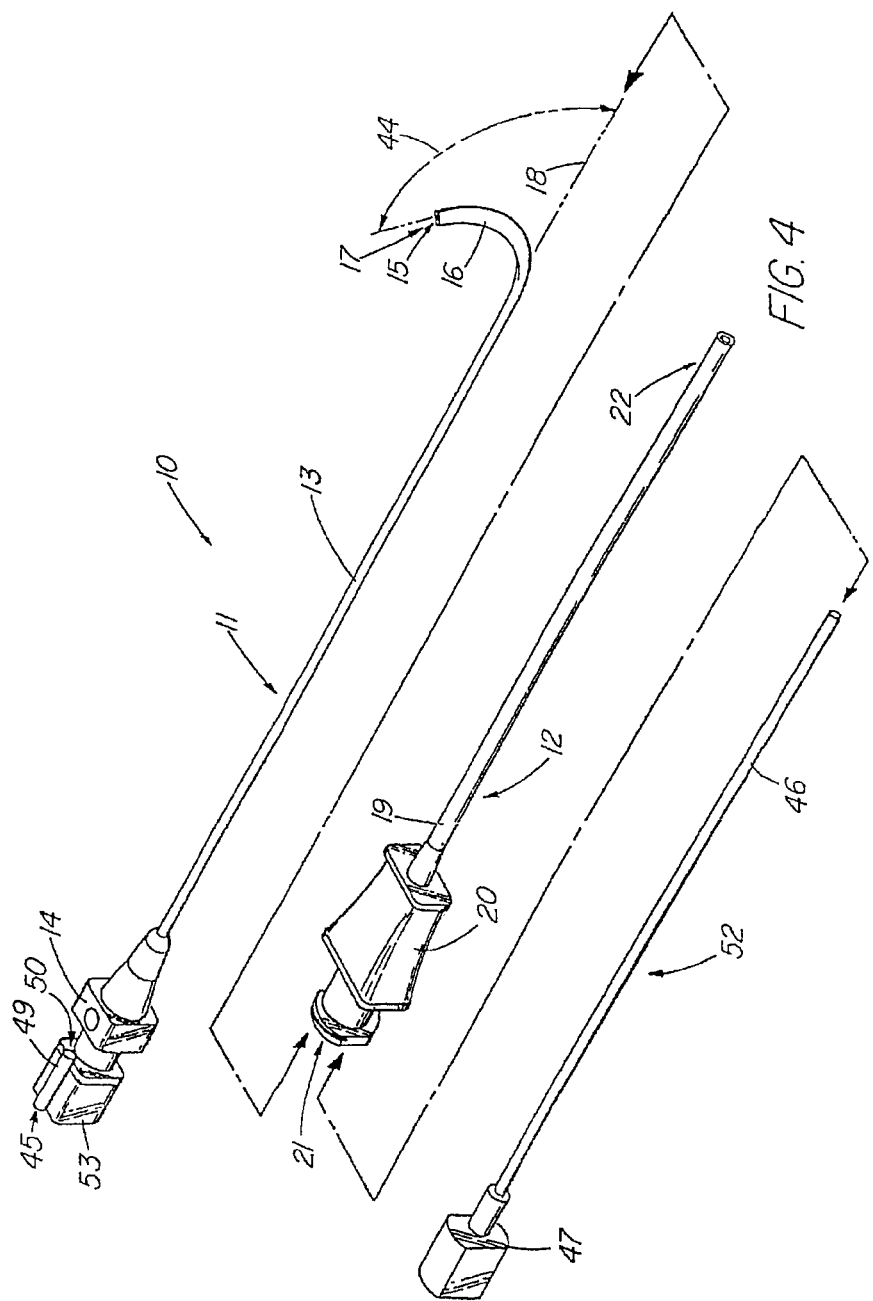
FIG. 4 is an exploded isometric view of a second embodiment of the inner and outer cannula.

FIG. 4 depicts a second version of the inner curved needle and sheathing outer needle adapted for use in the injection of medicaments, contrast media, or other non-viscous agents. The infusion needle 11 is comprised of a smaller gauge needle cannula 13, preferably around twenty-five (25) gauge, mounted to a proximal hub 14. The preformed bend 16 of individual needle cannula 13 has a slightly tighter radius than that illustrated in FIGS. 1 through 3.

Still referring to FIG. 4, the coaxial outer cannula 12 includes a correspondingly sized needle cannula 19, preferably around twenty-one (21) gauge, attached to a standard needle hub that is adapted to receive proximal hub 14 of infusion needle 11. The embodiment of FIG. 4 is used with a plurality of stylets that are inserted within both the inner and outer needles during their respective introduction into the body. The first is an outer cannula introducer stylet 52 that is inserted into the passageway 21 of coaxial outer cannula 12. The coaxial outer cannula 12 and outer cannula introducer stylet 52 are inserted together into the patient. The stylet, which is preferably a stainless steel stylet wire 46 with an attached standard plastic needle hub 47, prevents the coaxial outer cannula 12 from coring tissue into passageway 21 at distal tip 22.

Once coaxial outer cannula 12 is in position, outer cannula introducer stylet 52 is withdrawn from coaxial outer cannula 12 and infusion needle 11 and second introducer stylet 45 are inserted together into outer needle passageway 21. The inner needle introducer stylet 45, which is longer than outer cannula introducer stylet 52 in order to fit the longer infusion needle 11, serves a similar function to the outer cannula introducer stylet 52 by preventing coring of tissue when infusion needle 11 is deployed from coaxial outer cannula 12.

Figure 5:
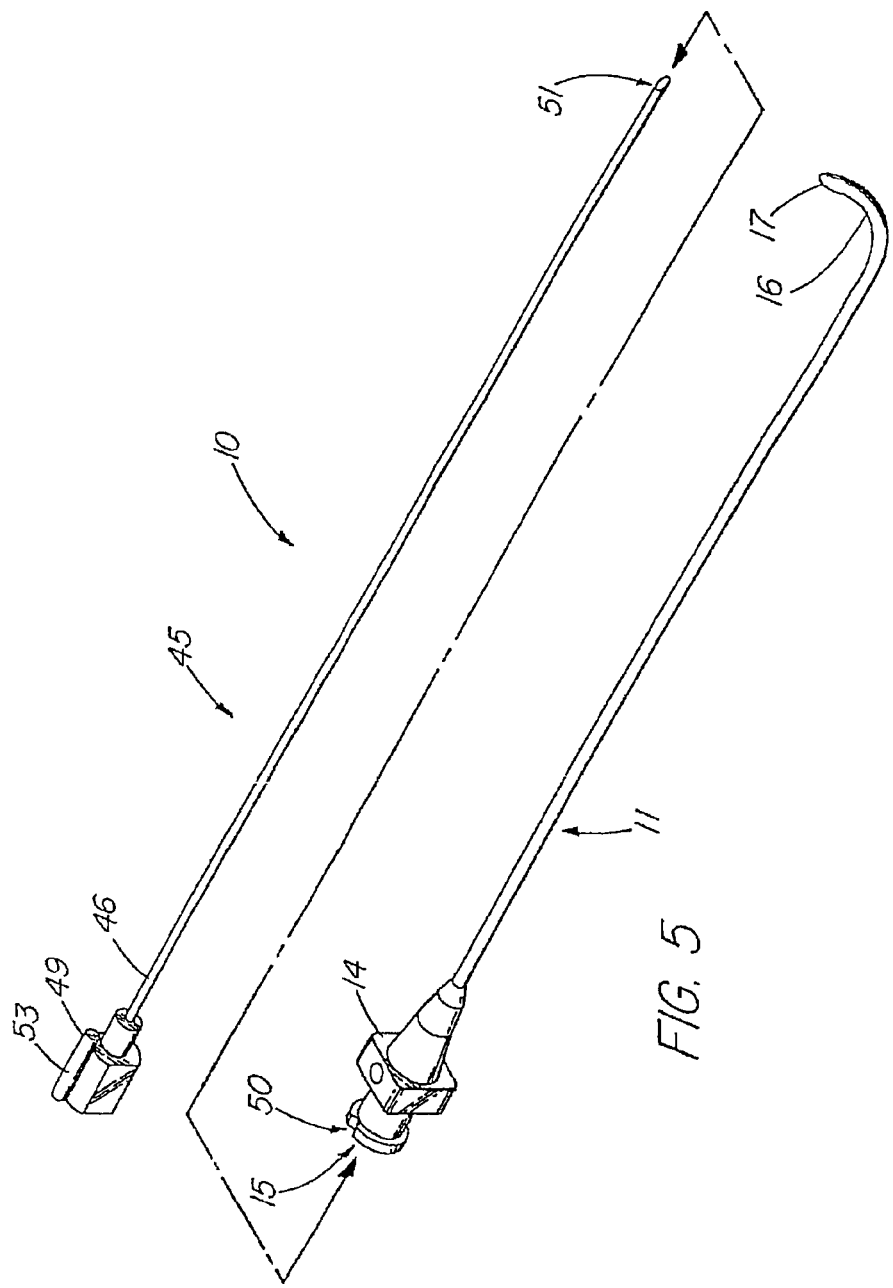
FIG. 5 depicts a pictorial view of the inner cannula of FIG. 4 with an introducer stylet.

As illustrated in FIGS. 4 and 5, proximal hub 14 of infusion needle 11 is adapted such that hub 53 of inner needle introducer stylet 45 locks together with proximal hub 14 to keep the two in alignment. This locking mechanism includes a molded protuberance 49 on hub 53 that fits within a recess 50 on proximal hub 14. The purpose of maintaining alignment of hub 53 and proximal hub 14 is to match the beveled surface 51 at the tip of the inner needle introducer stylet 45, shown in FIG. 5, with the beveled edge at the tip 17 of infusion needle 11.

Figure 8:
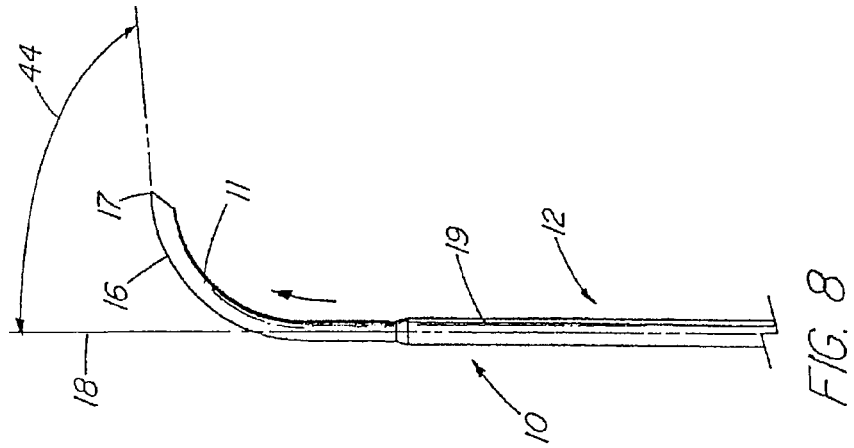
FIG. 8 is a side view of the inner cannula of FIG. 4 being still further deployed from the outer cannula.
Figure 7:
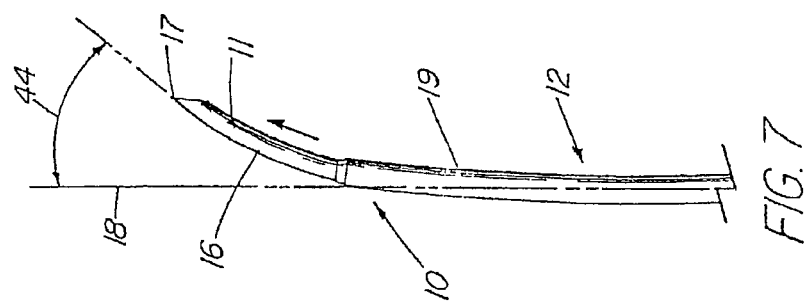
FIG. 7 is a side view of the inner cannula of FIG. 4 being further deployed from the outer cannula.
Figure 6:
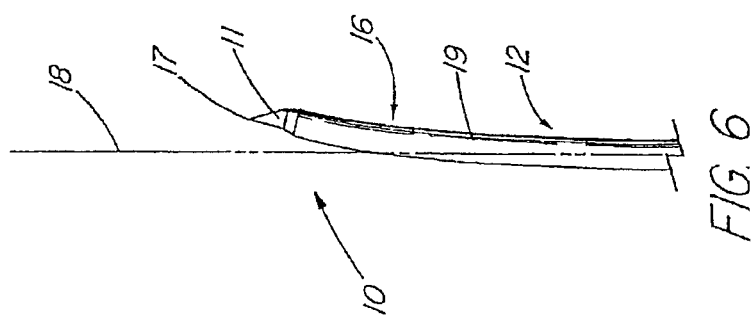
FIG. 6 is a side view of the inner cannula of FIG. 4 being initially deployed from the outer cannula.

FIGS. 6 through 8 depict the deployment of infusion needle 11 from within outer needle cannula 12. FIG. 6 shows infusion needle 11 during initial deployment from coaxial outer cannula 12. The preformed bend 16 of the infusion needle 11 is constrained by the cannula 19; however, as illustrated in FIG. 6, preformed bend 16 may be of sufficient stiffness to slightly deform outer cannula 19 while infusion needle 11 is inside coaxial outer cannula 12. Despite this slight deformation, coaxial outer cannula 12 is still substantially straight.

As depicted in FIG. 7, stress preformed bend 16 places on outer cannula 19 relaxes as infusion needle 11 is further deployed and the angle of deflection 44 (measured from longitudinal axis 18 of coaxial outer cannula 12 to the opening at tip 17 of infusion needle 11) is increased. As infusion needle 11 is further deployed as depicted in FIG. 8, fully exposing preformed bend 16 to produce the largest angle of deflection 44, the unstressed outer cannula returns to a straight configuration.

The phenomenon depicted in FIGS. 6 through 8 is most noticeable when using smaller gauge cannulae, such as shown in FIGS. 4 and 5. The larger gauge outer cannula of FIGS. 1 to 3 is more resistant to deformation than that of FIGS. 4 and 5. Naturally, the tendency of the stressed outer cannula to deform is also very much dependent on the stiffness and radius of the preformed bend 16 as well as the thickness of the cannula wall and material used. To eliminate this deformation during introduction of the device into the body, stylet 45, as depicted in FIG. 5, can be used as a stiffener until removed immediately before the portion having preformed bend 16 is deployed.

FIGS. 9 through 11 depict the use of the device illustrated in FIG. 3 to perform a vertebroplasty procedure on a pathological vertebral body 33 using a transpedicular approach. As depicted in FIG. 9, coaxial outer cannula 12 with introducer trocar 25 is introduced through the wall 38 and into the marrow 37 of the vertebral body 33. The transpedicular route of access places the needle between the mammillary process 34 and accessory process 35 of the vertebral arch 55. The vertebral arch 55 is attached posteriorly to the vertebral body 33 and together they comprise the vertebra 54 and form the walls of the vertebral foremen 36.

Once coaxial outer cannula 12 and inner introducer trocar 25 are within the internal region or marrow 37 of the vertebral body, trocar 25 is withdrawn from the coaxial outer cannula 12 and infusion needle 11 is inserted in its place. FIG. 10 depicts infusion needle 11 infusing bone cement 41, commonly methyl methacrylate, into vertebral body 33 to provide it with improved structural integrity. As depicted in FIG. 11, infusion needle 11 can be partially withdrawn or rotated to obtain more complete filling or to avoid the network of vertebral veins. Even though the vertebral body may not need to be completely filled, the density of marrow 37 would still necessitate a second transpedicular stick in the absence of the instant apparatus infusing cement within multiple planes within vertebral body 33. Upon completion of the procedure, infusion needle 11 is withdrawn back into coaxial outer cannula 12 and both are removed from vertebral body 33.

The utility of the hollow, curved superelastic needles is certainly not limited to procedures involving the spine. Such needles are useful at many sites within the body that might require straight access by a needle, followed by indirect or lateral infusion, aspiration, or sampling. For example, the inner needle could be adapted to take biopsy samples from dense tissue, such as a breast lesion, especially where indirect access is might be desirable.

Figure 12:
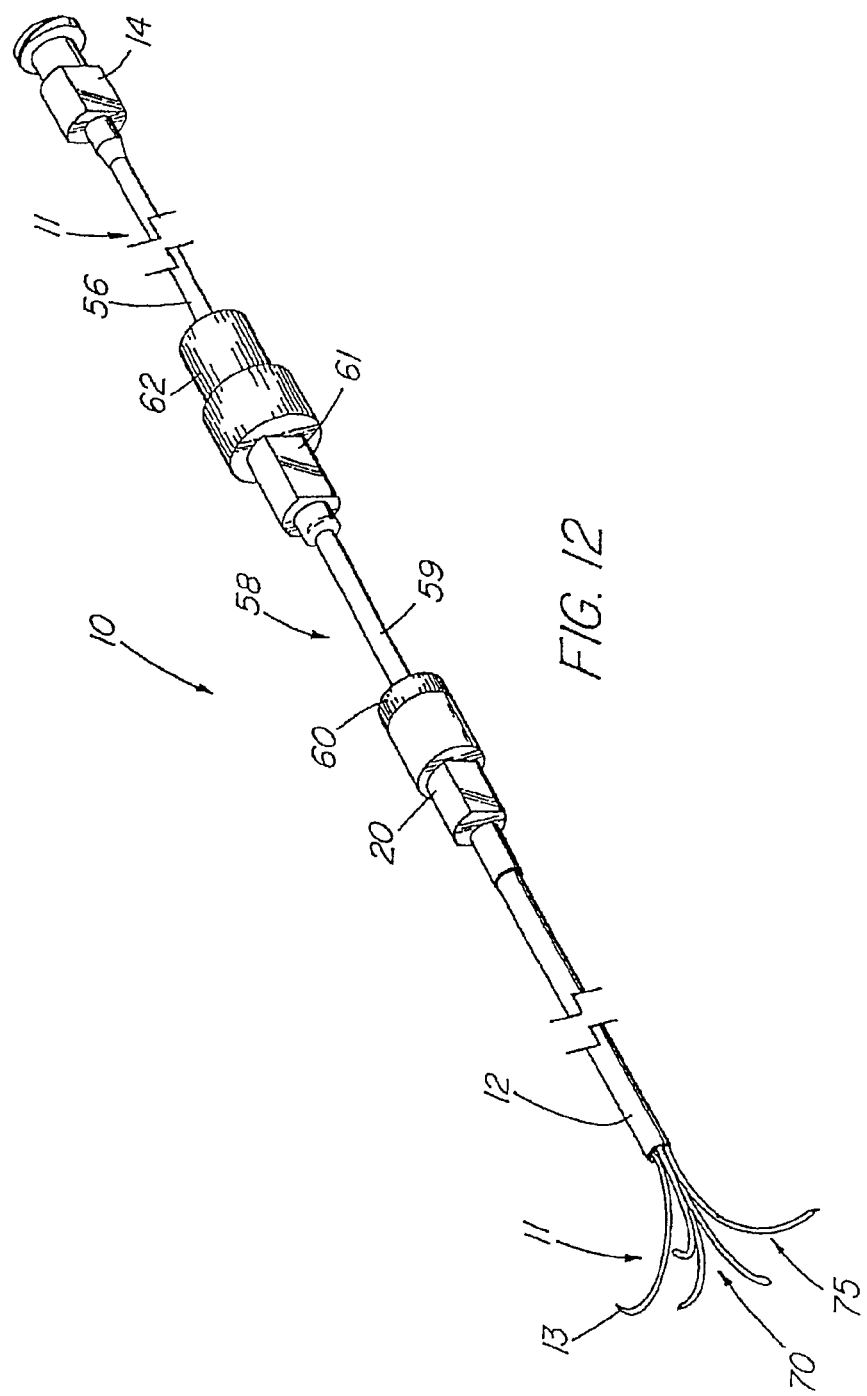
FIG. 12 is an isometric view of a third embodiment of the apparatus.

FIG. 12 is an isometric view of hollow, curved superelastic needles in which needle assembly 10 comprises a multiple needle assembly 70 useful in infusion of ethanol or other medicaments into a tumor. In FIG. 12, needle assembly 10 comprises an infusion needle 11, which includes a multiple needle assembly 70 comprising a plurality of needle cannulae 13, each having a preformed bend 16, a proximal assembly 58 for constraining the multiple needle assembly 70, and a coaxial outer cannula 12 for introducing the multiple needle assembly 70 to its anatomical target.

The multiple needle assembly 70 in FIG. 13 includes a base cannula 56 affixed to a proximal hub 14 such as a standard female luer fitting. A plurality of needle cannulae 13 are manifolded into base cannula 56, preferably evenly spaced in an umbrella configuration 75, and affixed in place with a solder joint 57. In the structure illustrated in FIG. 12, five needle cannulae 13 are used; from two to as many as appropriate for the given cannula size can be used. As with the other versions, needle cannulae 13 are preferably made of Nitinol that is either annealed or cold-worked to produce the preformed bend 16. In the structure illustrated in FIG. 12, the coaxial outer cannula 12 has an outer diameter of approximately 0.072 inches and an inner diameter of around 0.06 inches, while the individual curved needle cannulae 13 have an outer diameter of 0.02 inches and an inner diameter of about 0.12 inches. As shown in FIG. 14, the tips 17 of the needle cannulae 13 may be beveled to better penetrate tissue.

Deployment of curved needle cannulae 13 of multiple needle assembly 70 is depicted in FIG. 14. Needle cannulae 13 are restrained by coaxial outer cannula 12 until multiple needle assembly 70 is advanced, exposing the distal end portions of needle cannulae 13 at distal end 22 of coaxial outer cannula 12, whereby they radiate outward to assume, when fully advanced, the umbrella configuration 75 shown in FIG. 13.

FIG. 15 depicts a side view of an outer needle assembly comprising a coaxial outer cannula 12 and outer cannula introducer stylet 52 used in placement of the multiple needle assembly 70 of FIGS. 12 through 14. The outer cannula introducer stylet 52 is inserted into passageway 21 of coaxial outer cannula 12 with the male proximal hub 47 of the outer cannula introducer stylet 52 fitting into the female proximal hub 20 of coaxial outer cannula 12 when the outer cannula introducer stylet 52 is fully advanced. Outer cannula introducer stylet 52 includes a sharp tip 63, such as the diamond-shape tip depicted, for penetrating tissue.

The outer cannula introducer stylet 52 and coaxial outer cannula 12 may be introduced percutaneously into the liver or kidney and placed at the desired treatment location. The outer cannula introducer stylet 52 is then removed. The proximal assembly 58 with the preloaded multiple needle assembly is then advanced into the coaxial outer cannula 12 which remains in the patient. In the version illustrated in FIGS. 12 through 15, the coaxial outer cannula preferably has an outer diameter of about 0.095 inches and an inner diameter of about 0.076 inches, while the outer diameter of the inner stylet is preferably about 0.068 inches.

FIG. 16 a side view of the proximal assembly 58 shown of FIG. 12. The Proximal assembly 58 includes a distal male adaptor 60 connected to an intermediate cannula 59 that is sufficiently large to accommodate multiple needle assembly 70. At the proximal end of the intermediate cannula 59 is proximal assembly female adaptor 61 which is connected proximally to a proximal assembly hub 62, such as a Tuohy-Borst adaptor. Proximal assembly hub 62 is utilized by the physician during manipulation of the device.

The multiple needle assembly 70 of FIG. 13 is loaded into lumen 64 at the proximal end 65 of the proximal assembly hub 62, with the needle cannulae 13 remaining within intermediate cannula 59. Distal end 66 of proximal assembly 58 with preloaded multiple needle assembly 70 is then inserted into proximal hub 20 of the coaxial outer cannula as depicted in FIG. 12. The multiple needle assembly 70 is then advanced from the proximal assembly 58 into the coaxial outer cannula 12 where it is deployed as depicted in FIGS. 12 to 14. Ethanol is infused into multiple needle assembly 70 via the proximal hub 14 of the infusion needle 11. Following treatment, the multiple needle assembly 70 is withdrawn into coaxial outer cannula 12 and the entire needle assembly 10 is removed from the patient.

FIGS. 21 and 22 depict a variation of needle assembly 10 of FIG. 12 in which infusion needle 11 and coaxial outer cannula 12 are connected to a coaxial handle 76 used to advance and deploy multiple needle assembly 70 releasably from constraint of coaxial outer cannula 12. As shown, coaxial handle 76 comprises a stationary outer component 77 that fits over base cannula 56 of multiple needle assembly 70 and attaches to proximal hub 20. A slidable inner component 78 further comprises a thumb piece 79 used by the physician to advance or retract the coaxial outer cannula 12 as the slidable inner component 78 retracts into stationary outer component 77.

In FIG. 21, the needle assembly is depicted in the introducer position with the thumb piece 79 advanced fully forward within a slot 80 in outer slidable component 77.

FIG. 22 depicts the deployment state of needle assembly 10 in which thumb piece 79 has been moved to the most proximal position within slot 80. In this position, coaxial outer cannula 12 is retracted to fully expose the plurality of needle cannulae 13 which can assume their unconstrained configuration with the preformed bends 16.

This type of handle can be used with both the multiple and single infusion needle where a introducer trocar or stylet is not required. Other well-known types of coaxial handles 76 include, but are not limited to, screw-type, rachet-type, or trigger-activated handles which allow coaxial outer cannula 12 to be longitudinally displaced relative to infusion needle 11. To reduce the need for a trocar or stylet for facilitating tissue penetration, distal tip 22 of coaxial outer cannula 12 can be shaped into a needle point such as depicted, or into a non-coring point to help maintain an open outer cannula passageway 21.

A syringe or other reservoir container can be attached to proximal hub 14 as an infusate source or for collection of aspirated material. In addition, a reservoir, such as a syringe, can be incorporated internally within coaxial handle 76 of needle assembly 10 or integrally attached thereto.

Another version of multiple needle assembly 70 is depicted in FIGS. 17-20 whereby there are one or more groupings of proximally-located needles 73 in addition to the distally-located needles 74 that are similar to those illustrated in of FIG. 12. By locating the additional needle cannulae 13 proximal to those at the distal end, wider dispersal and coverage is attained for infusion of medicaments.

Figure 17:
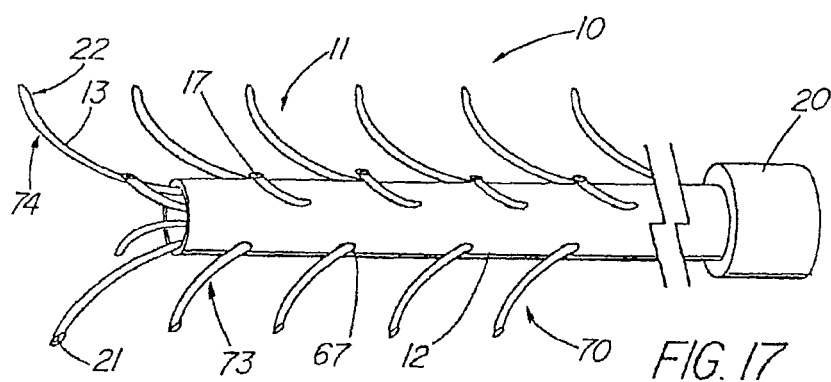
FIG. 17 is a side view of a fourth embodiment of the apparatus.

In the version illustrated in FIG. 17, there is an arrangement of four needle cannulae comprising the distally-located needles 74, while at least one other group comprising proximally-located needles 73 located along the length of infusion needle 11 provides for simultaneous infusion in a more proximal location. The needle cannulae 13 of the proximally-located and distally-located needles 73, 74 can vary in configuration, length, number, and how they are attached to a base cannula 56 such as that shown in FIG. 13. For example, individual needle cannulae 13 within an umbrella configuration 75 or between proximally-located and distally-located needles 73, 74 can be longer, or have a different radius than others, to vary the distribution pattern of the infusate.

Figure 18:
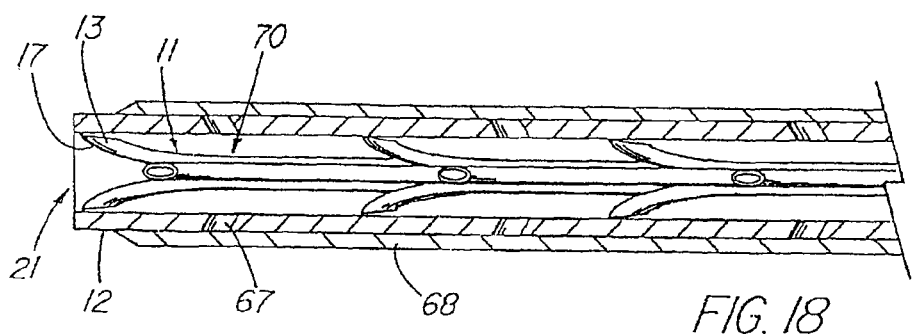
FIG. 18 is a broken, partially-sectioned side view of the apparatus illustrated in FIG. 17 prior to deployment.

As depicted in FIGS. 17 and 18, each pair of oppositely-disposed needle cannulae 13 within a grouping of four proximally-located needles 73 are longitudinally offset with respect to the adjacent pair located ninety degrees (90° therefrom, as are the side apertures 67 from which they emerge. With regard to attachment, possibilities include, but are not limited to, having all needle cannulae 13 attaching to a single base cannula 56; dividing base cannula 56 such that a separate portion extends distally from the proximally-located needles 73 to join the distally-located needles 74, or eliminating the base cannula 56 such that needle cannulae 13 of multiple needle assembly 70 are separate and run the length of infusion needle 11.

To constrain needle cannulae 13 for introduction along a single pathway into the body, a coaxial outer cannula 12 is used that has side apertures 67 in the cannula to permit the proximally-located needles 73 to deploy outward therethrough for lateral infusion. FIG. 18 shows a sectioned view of the needle assembly of FIG. 17 in which the needle cannulae 13 are constrained in the introduction position. An introducer cannula 68 is used to selectively expose side apertures 67 in versions where the arrangement of needles is such that individual needle cannulae 13 may prematurely exit a non-designated hole or row, preventing or delaying proper deployment of the multiple needle assembly 70. By maintaining the introducer sheath over side apertures 67 until distally-located needles 73 are deployed, proper deployment of all needle cannulae 13 is easier.

Figure 19:
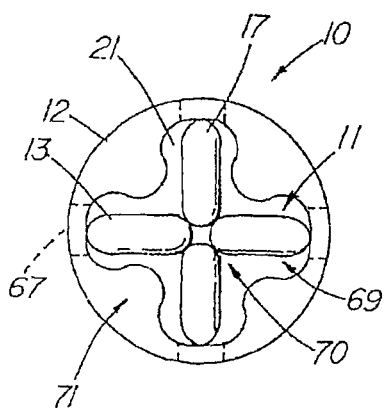
FIG. 19 is a transverse cross-sectional view of coaxial outer cannula depicted in FIG. 17.
Figure 20:
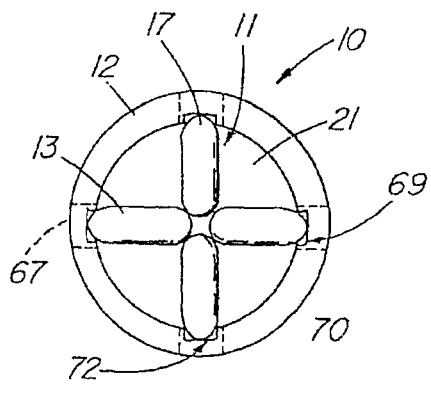
FIG. 20 depicts cross-sectional views of two embodiments of coaxial outer cannula depicted in FIG. 17.

FIGS. 19 and 20 illustrate intraluminal guides 69 to help facilitate proper alignment of needle cannulae 13 with a designated side aperture 67. In FIG. 19, a series of ridges 71 within passageway 21 of coaxial outer cannula 12 guide the needle cannulae 13 to align with a designated side aperture 67. FIG. 20 depicts an alternative intraluminal guide 69 in which the needle cannulae 13 travel longitudinally within grooves 72 formed in the inner wall of passageway 21.

What is claimed is:

1. A needle assembly, comprising:
    an outer needle cannula having a distal opening;
    a multi-needle subassembly received within said outer needle cannula, said subassembly comprising a base cannula and a plurality of needle cannulae having proximal portions manifolded into and affixed in place within said base cannula to fix distal tip portions of said needle cannulae in an array extending distally of a distal end of said base cannula, said multi-needle subassembly slidable within said outer needle cannula to selectively deploy said array from said distal opening of said outer needle cannula; and
    said needle cannulae each having a passageway, and each said needle cannula, while in its unconstrained configuration, having at least one preformed bend proximate to said distal tip portion and being constrainable to a second configuration, whereby at release of external constraining forces, said distal tip portion of each said needle cannula substantially returns to the unconstrained configuration extending forwardly and radially outwardly from a respective said preformed bend.

2. The needle assembly of claim 1, wherein each of said needle cannulae comprises a superelastic Ni—Ti alloy.

3. The needle assembly of claim 1, wherein each of said needle cannulae has a distal tip that is deflected at an angle between about 30° and about 110° when in an unconstrained condition.

4. The needle assembly of claim 3, wherein the at least one preformed bend of each needle cannula of said plurality of needle cannulae is induced by mechanical deformation of the needle cannula such that the superelastic material of the at least one preformed bend includes a martensitic crystalline structure, while non-mechanically deformed portions of the needle cannula comprise a substantially austenitic crystalline structure.

5. The needle assembly of claim 1, wherein each of said needle cannulae has a distal tip that is deflected at an angle between about 60° and about 90° when in an unconstrained condition.

6. The needle assembly of claim 1, also comprising an outer needle cannula containing said plurality of needle cannulae.

7. The needle assembly of claim 6, wherein said outer needle cannula has side apertures, with each of said plurality of needle cannulae having a distal portion configured to exit one of said side apertures.

8. A method of infusing a medicament into a tumor, comprising passing the medicament through the passageways of a needle assembly of claim 1.

9. The method of claim 8, wherein the medicament comprises ethanol.

10. A needle assembly, comprising:
an outer needle cannula having a distal opening;
a multi-needle subassembly received within said outer needle cannula, said subassembly comprising a base cannula and a plurality of needle cannulae having proximal portions manifolded into and affixed in place within said base cannula to fix distal tip portions of said needle cannulae in a needle array extending distally of a distal end of said base cannula, said multi-needle subassembly slidable within said outer needle cannula to selectively deploy said needle array from said distal opening of said outer needle cannula; said needle cannulae each having a passageway, and each said needle cannula, while in its unconstrained configuration, having at least one preformed bend proximate to said distal tip portion and being constrainable to a second configuration, whereby at release of external constraining forces, said distal tip portion of each said needle cannula substantially returns to the unconstrained configuration extending forwardly and radially outwardly from a respective said preformed bend;
a proximal base cannula hub fixed to said base cannula and configured to infuse material or aspirate material through the needle cannulae and the base cannula;
an outer needle cannula hub fixed to said outer needle cannula;
a handle including a stationary outer component attached to the proximal base cannula hub and a slidable inner component attached to the outer needle cannula hub, wherein the slidable inner component is slidable into the stationary outer component to deploy said needle array from said distal opening of said outer needle cannula, and slidable out of said stationary outer component to retract said needle array into said distal opening of said outer needle cannula.

11. The needle assembly of claim 10, wherein each of said plurality of needle cannulae comprises a superelastic Ni—Ti alloy.

12. The needle assembly of claim 10, wherein each of said needle cannulae has a distal tip that is deflected at an angle between about 30° and about 110° when in an unconstrained condition.

13. The needle assembly of claim 10, wherein each of said needle cannulae has a distal tip that is deflected at an angle between about 60° and about 90° when in an unconstrained condition.

* * * * *